US008219207B2

(12) United States Patent
Olsen

(10) Patent No.: US 8,219,207 B2
(45) Date of Patent: Jul. 10, 2012

(54) THERMAL SWITCH FOR IMPLANTABLE MEDICAL DEVICES

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 667 days.

(21) Appl. No.: 11/683,907

(22) Filed: Mar. 8, 2007

(65) Prior Publication Data
US 2009/0105789 A1 Apr. 23, 2009

(51) Int. Cl.
A61N 1/08 (2006.01)
(52) U.S. Cl. .............. 607/63; 600/411; 600/412; 607/2; 607/102; 607/116
(58) Field of Classification Search .......... 607/2, 62–63, 607/102, 116; 600/411–412
See application file for complete search history.

(56) References Cited

U.S. PATENT DOCUMENTS

| 4,280,511 | A | * | 7/1981 | O'Neill | 607/122 |
| 4,328,812 | A | * | 5/1982 | Ufford et al. | 607/122 |
| 4,590,950 | A | * | 5/1986 | Iwaszkiewicz et al. | 607/119 |
| 4,907,589 | A |   | 3/1990 | Cosman | |
| 5,433,732 | A | * | 7/1995 | Hirschberg et al. | 607/7 |
| 5,447,533 | A | * | 9/1995 | Vachon et al. | 607/120 |
| 5,476,485 | A |   | 12/1995 | Weinberg et al. | |
| 5,596,995 | A |   | 1/1997 | Sherman et al. | |
| 5,676,162 | A | * | 10/1997 | Larson et al. | 128/899 |
| 5,844,464 | A | * | 12/1998 | Kalapodis et al. | 337/140 |
| 6,078,244 | A | * | 6/2000 | Quinn et al. | 337/140 |
| 6,132,426 | A | * | 10/2000 | Kroll | 606/41 |
| 6,421,567 | B1 | * | 7/2002 | Witte | 607/122 |
| 6,662,048 | B2 |   | 12/2003 | Balczewski et al. | |
| 6,892,095 | B2 |   | 5/2005 | Salo | |
| 7,047,074 | B2 |   | 5/2006 | Connelly et al. | |
| 2003/0011486 | A1 | * | 1/2003 | Ying | 340/825.69 |
| 2003/0013948 | A1 |   | 1/2003 | Russell | |
| 2003/0125774 | A1 |   | 7/2003 | Salo | |
| 2003/0167081 | A1 |   | 9/2003 | Zhu et al. | |
| 2004/0004464 | A1 | * | 1/2004 | Tsukamoto et al. | 320/162 |
| 2005/0197685 | A1 | * | 9/2005 | Russell | 607/115 |
| 2005/0222642 | A1 |   | 10/2005 | Przybyszewski et al. | |
| 2005/0222647 | A1 |   | 10/2005 | Wahlstrand et al. | |
| 2005/0222656 | A1 |   | 10/2005 | Wahlstrand et al. | |
| 2005/0222658 | A1 |   | 10/2005 | Hoegh et al. | |
| 2005/0222660 | A1 | * | 10/2005 | McAuliffe et al. | 607/122 |
| 2006/0089697 | A1 |   | 4/2006 | Cross, Jr. et al. | |

FOREIGN PATENT DOCUMENTS

| EP | 1 779 869 A1 | 5/2007 |
| WO | WO 2005/102446 A1 | 11/2005 |
| WO | WO 2006/064430 A1 | 6/2006 |

OTHER PUBLICATIONS

Helfer et al., "Can pacemakers, neurostimulators, leads, or guide wires be MRI safe? Technological concerns and possible resolutions," *Minimally Invasive Therapy*, 2006, pp. 114-120, vol. 15, No. 2.
International Search Report for Application No. PCT/US2007/066356, date of mailing Feb. 21, 2008, 4 pages.

* cited by examiner

*Primary Examiner* — Carl H Layno
*Assistant Examiner* — Jennifer Ghand

(57) ABSTRACT

An implantable medical device includes an electrode having a thermal switch. The thermal switch is configured to electrically decouple components of the implantable medical device when in contact with tissue at temperatures above normal body temperature.

20 Claims, 6 Drawing Sheets

THERMAL SWITCH FOR IMPLANTABLE MEDICAL DEVICES

BACKGROUND

The present application relates generally to the field of implantable medical devices. More particularly, the present application relates thermal switches for neurostimulation devices, pacemakers, implantable defibrillators, and other implantable medical devices.

Implantable neurological stimulation devices (sometimes referred to as an implantable neurostimulator or INS) generate electrical stimulation signals that are used to influence the human nervous system or organs. Conventionally, the INS has been surgically implanted into a patient in a subcutaneous pocket in the abdomen, pectoral region, or upper buttocks area. Electrical contacts carried on the distal end of a lead are placed at the desired stimulation site (e.g., at a location in the spine or directly in the brain) and the proximal end of the lead is connected to the INS. The lead typically has one or more insulated electrical conductors (filar) that connect the electrical contacts, or electrodes, to the INS. For neurostimulation of the spine or brain, the leads may typically have 4 or 8 sets of conductors and electrodes.

It may be desirable to implant the INS at a location in the patient's head in cases where the distal end of the lead is provided at a site directly in the brain. For example, it may be desirable to implant the INS under the scalp on top of the patient's head (either on top of the surface of the skull or in a pocket formed in the skull).

Deep brain stimulation implants may be used for the treatment of a variety of diseases including epilepsy and Parkinson's Disease. In these devices, the electrodes are implanted in the brain of the patient to provide electric stimulation to affected regions of the brain.

Alternatively, the leads may be placed in the epidural region of the spine to stimulate the dorsal horn of the spinal cord for the treatment of pain, or other diseases such as angina.

These patients may also require diagnostic procedures to monitor the progression of their disease, or to aid in the diagnosis of unrelated injuries or disorders. Some increasingly common diagnostic procedures involve the use of magnetic resonance imaging (MRI). MRI systems use radio frequency radiation in the presence of a strong magnetic field to produce diagnostic images of the patient.

One problem that arises is tissue heating when the leads are exposed to RF electromagnetic fields. The leads act like antennas and absorbs energy which will be dissipated as RF currents at the electrodes. The RF currents will oscillate the water molecules near the electrodes at high frequency and cause the tissue to heat. If the amount of heating is greater than the tissue will tolerate, the tissue will be damaged. The RF heating may be especially problematic in environments such as in MRI systems where RF is used. Generally, increases in tissue temperature can lead to tissue damage. Some literature has shown the potential for heating in excess of 30° C. Helfer et al., *Minimally Invasive Therapy,* 2006; 15:2; 117-120.

Accordingly, there is a need to provide a stimulation lead or an implantable medical device such as an INS that will not cause unacceptable tissue heating when exposed to RF. There is further a need to provide an improved implantable medical device that utilizes a lead which disconnects the conductor(s) from the electrode(s) during and an MRI to avoid overheating. If a thermally activated switch is placed adjacent to or inside of the electrode, the RF energy in the lead will not be allowed to dissipate thru the electrodes and overheat the tissue, since the switch will open the circuit before the tissue overheats.

DETAILED DESCRIPTION

According to an exemplary embodiment, an implantable medical device (e.g., an INS) is provided that includes an electrode that is configured to avoid overheating. The electrode having a thermal switch may be included in several types of implantable medical devices.

Figure 1:
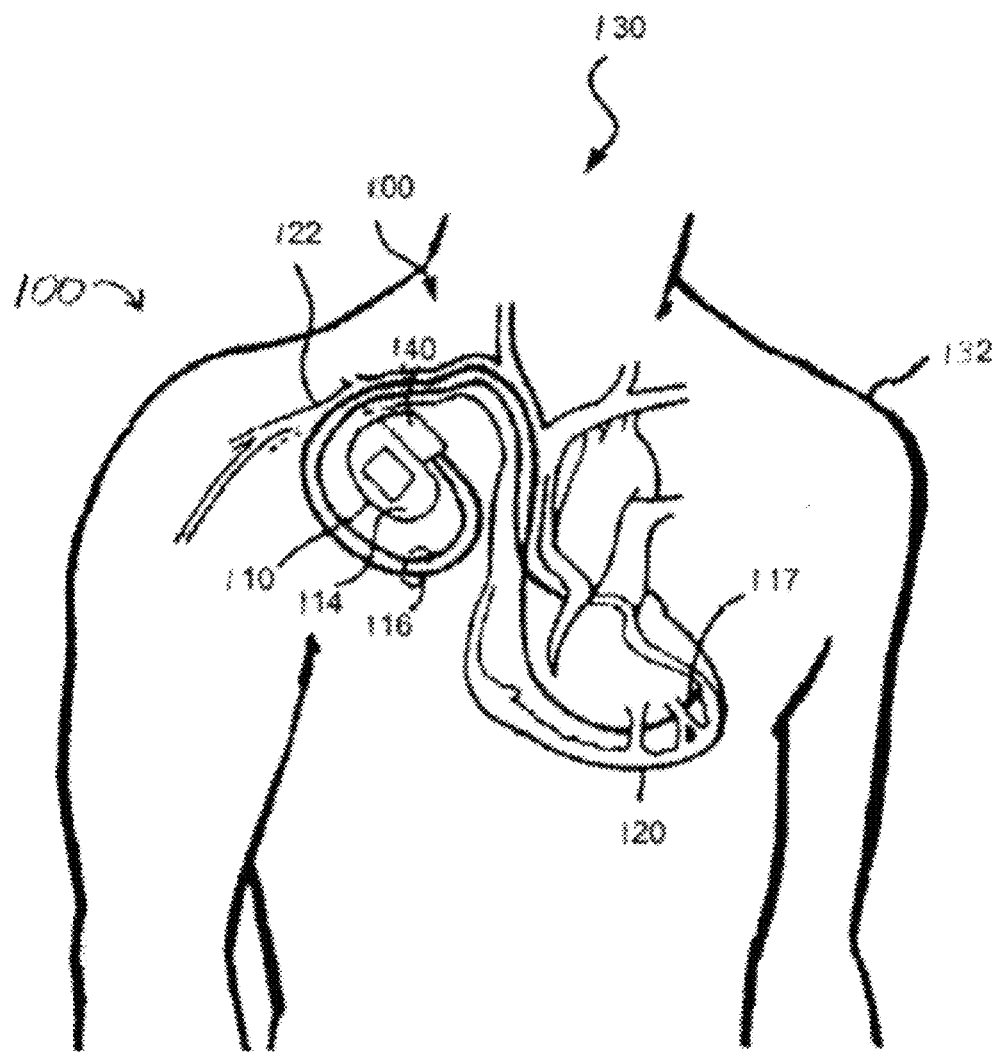
FIG. 1 is a schematic view of an implantable medical device placed in a human body.

FIG. 1 illustrates a schematic view of a system 100 (e.g., an implantable medical device) implanted within a body or torso 132 of a patient 130. The system 100 may include electrodes having thermally sensitive switches. The system 100 includes a device 110 in the form of an implantable medical device that for purposes of illustration is shown as a defibrillator configured to provide a therapeutic high voltage (e.g., 700 volt) treatment for the patient 130.

The device 110 includes a container or housing 114 that is hermetically sealed and biologically inert according to an exemplary embodiment. The container may be made of a conductive material. One or more leads 116 electrically connect the device 110 and to the patient's heart 120 via a vein 122. Electrodes 117 are provided to sense cardiac activity and/or provide an electrical potential to the heart 120. At least a portion of the leads 116 (e.g., an end portion of the leads shown as exposed electrodes 117) may be provided adjacent or in contact with one or more of a ventricle and an atrium of the heart 120.

The device 110 includes a battery 140 provided therein to provide power for the device 110. The size and capacity of the battery 140 may be chosen based on a number of factors, including the amount of charge required for a given patient's physical or medical characteristics, the size or configuration of the device, and any of a variety of other factors. According to an exemplary embodiment, the battery is a 5 mAh battery. According to another exemplary embodiment, the battery is a 300 mAh battery. According to various other exemplary embodiments, the battery may have a capacity of between approximately 10 and 1000 mAh.

Figure 2:
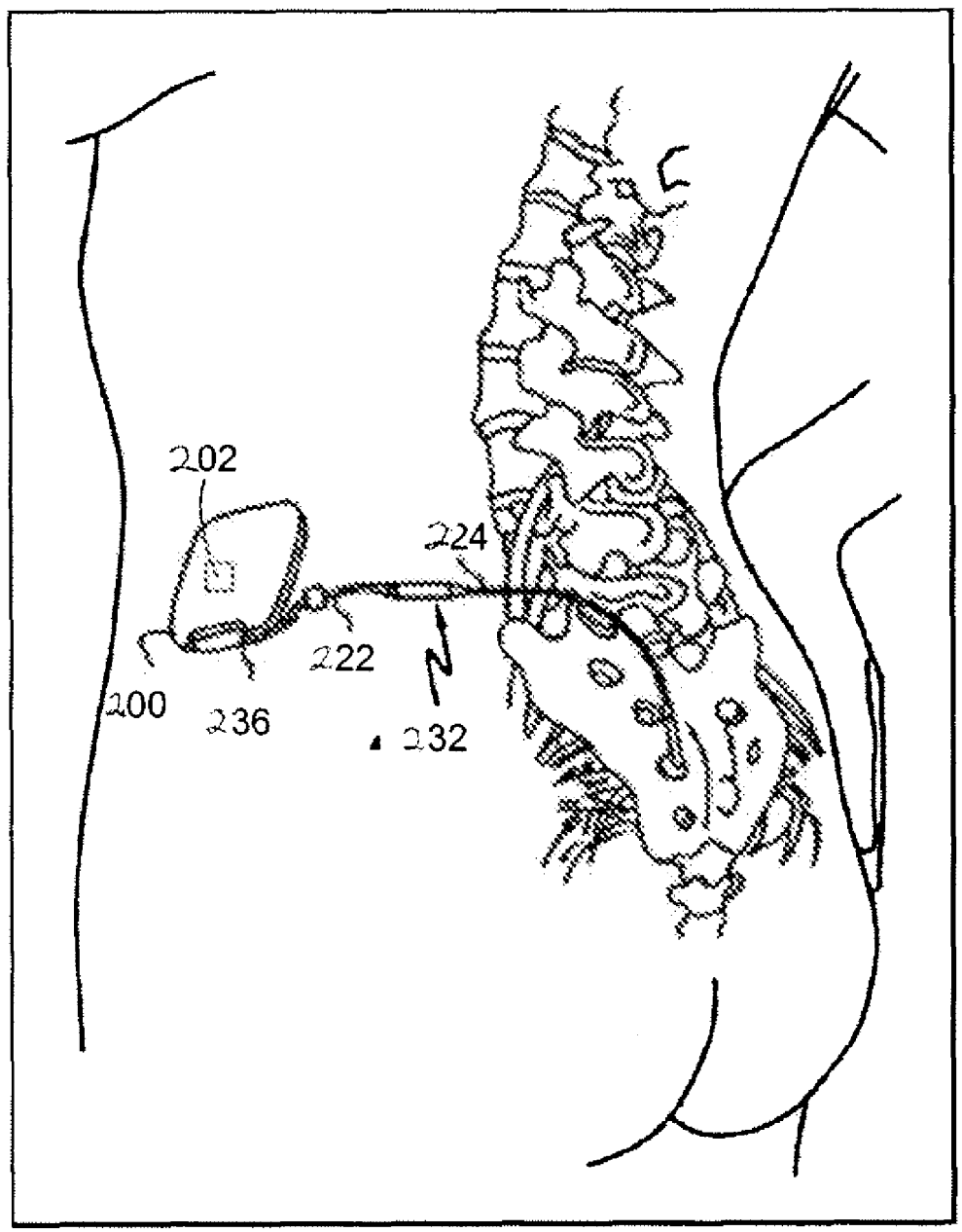
FIG. 2 is a schematic view of another implantable medical device placed in a human body.

According to another exemplary embodiment shown in FIG. 2, an implantable neurological stimulation device 200 (an implantable neurostimulator or INS) may include a battery 202 such as those described above with respect to the various exemplary embodiments. Examples of some neurostimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 200 includes a lead extension 222 and a stimulation lead 224. The stimulation lead 224 is one or more insulated electrical conductors with a connector 232 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and some stimulation leads are designed to be surgically implanted, such as the Model 3998 Specify® lead also available from Medtronic.

Although the lead connector 232 can be connected directly to the INS 500 (e.g., at a point 236), typically the lead connector 232 is connected to a lead extension 222. The lead extension 222, such as a Model 7495 available from Medtronic, is then connected to the INS 200.

Implantation of an INS 220 typically begins with implantation of at least one stimulation lead 224, usually while the patient is under a local anesthetic. The stimulation lead 224 can either be percutaneously or surgically implanted. Once the stimulation lead 224 has been implanted and positioned, the stimulation lead's 224 distal end is typically anchored into position to minimize movement of the stimulation lead 224 after implantation. The stimulation lead's 224 proximal end can be configured to connect to a lead extension 222.

The INS 200 is programmed with a therapy and the therapy is often modified to optimize the therapy for the patient (i.e., the INS may be programmed with a plurality of programs or therapies such that an appropriate therapy may be administered in a given situation).

A physician programmer and a patient programmer (not shown) may also be provided to allow a physician or a patient to control the administration of various therapies. A physician programmer, also known as a console programmer, uses telemetry to communicate with the implanted INS 200, so a clinician can program and manage a patient's therapy stored in the INS 200, troubleshoot the patient's INS 200 system, and/or collect data. An example of a physician programmer is a Model 7432 Console Programmer available from Medtronic. A patient programmer also uses telemetry to communicate with the INS 200, so the patient can manage some aspects of her therapy as defined by the clinician. An example of a patient programmer is a Model 7434 Itrel® 3 EZ Patient Programmer available from Medtronic.

Figure 3:
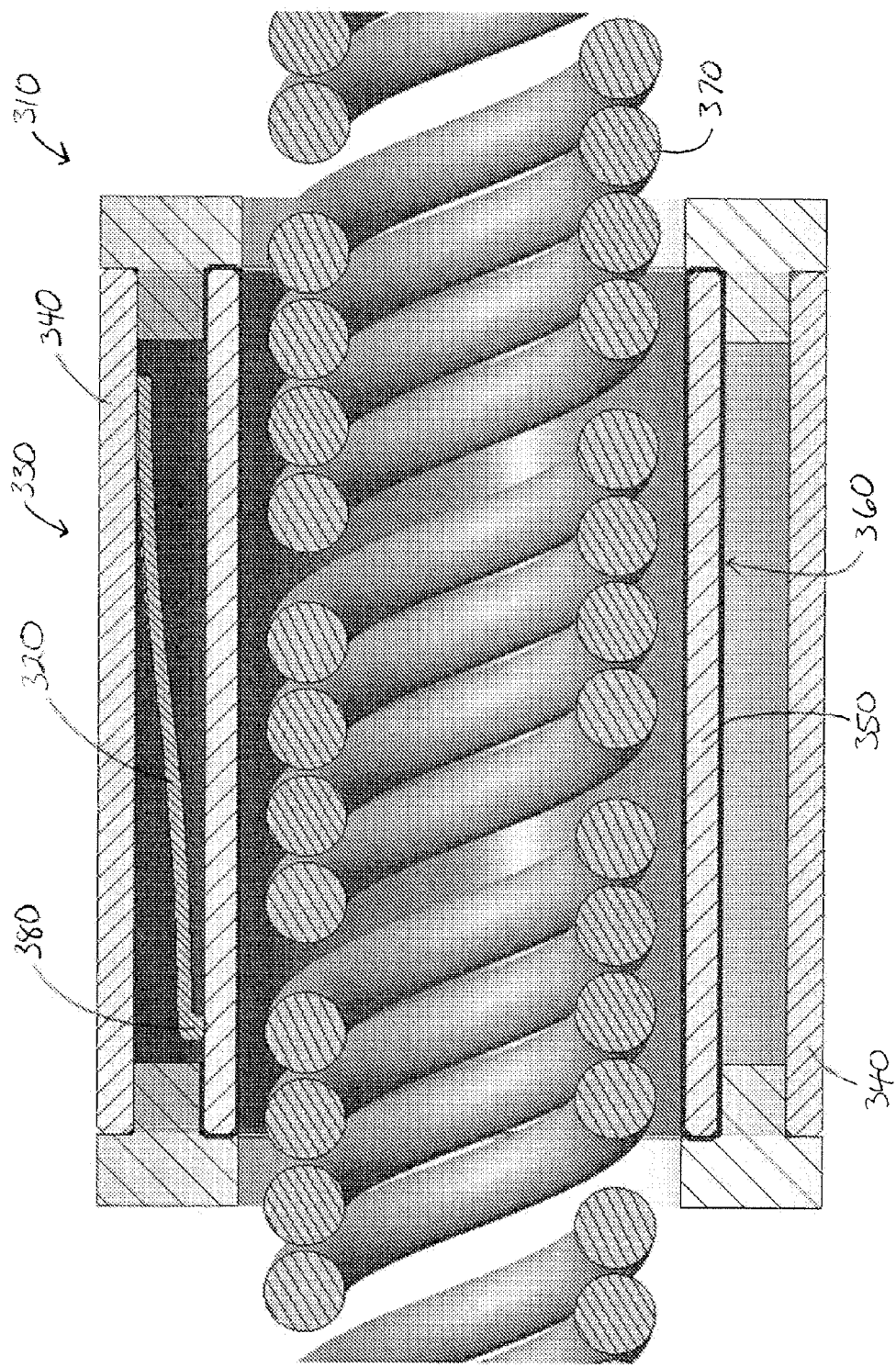
FIG. 3 is longitudinal cross-sectional view of a lead for use in an implantable medical device.
Figure 4:
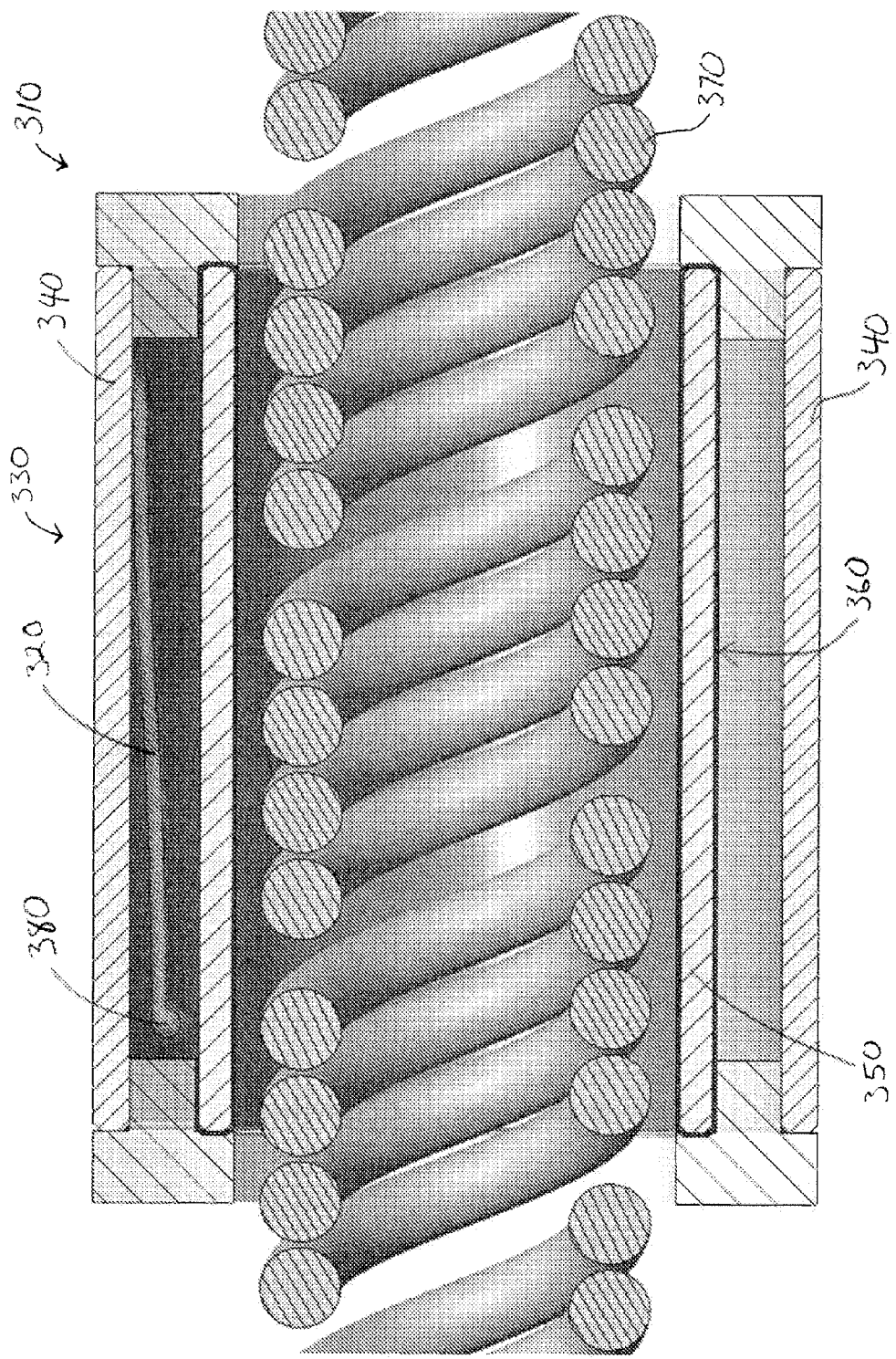
FIG. 4 is longitudinal cross-sectional view of a lead for use in an implantable medical device.

FIGS. 3 and 4 illustrate a lead 310 for an implantable medical device including a thermally responsive switch 320. Lead 310 includes an electrode segment 330 comprising an outer ring 340 and an inner ring 350. Inner ring 350 may include an isolating coating 360. Lead filars 370 extend through the lead 310. In the embodiment shown, four lead filars 370 are wound through into a helical shape. The pitch, helix diameter, and filar diameter are selected to provide a desired impedance and other electrical properties.

Thermal switch 320 extends from the inner surface of outer ring 340 towards the outer surface of inner ring 350. Alternatively, thermal switch 320 may be fixedly coupled to inner ring 350 and extend towards outer ring 340. Thermal switch 320 includes a contact portion 380 that is configured to come in contact with a portion of the outer surface of inner ring 350. The portion of the outer surface of the inner ring configured to contact the contact portion 380 is not covered by the isolating coating 360.

As shown in FIG. 3, thermal switch 320 is fixedly coupled to the inner surface of outer ring 340 and extends longitudinally in relation to lead 310. Contacting portion 380 is formed a free end of thermal switch 320 at a point distal to the point where thermal switch 320 is fixedly coupled to the inner surface of outer ring 330. Thermal switch 320 may comprise a bimetallic strip. The metals selected for the bimetallic strip are selected such that the two metals are suitable for use in the human body, and the coefficients of thermal expansion of the two metals is sufficiently different to provide a switch that deflects with a change in temperature. Table 1 provides a list of metals and their coefficients of thermal expansion at room temperature.

TABLE 1

| Material | Coefficient of Thermal Expansion ($10^{-5}/°$ C.) |
| --- | --- |
| Zinc | 1.9-3.5 |
| Aluminum | 2.6-2.9 |
| Silver | 2.0 |
| Cr—Ni—Fe Alloys | 1.7-1.9 |
| Stainless Steel | 1.1-1.9 |
| Cr—Ni—Co—Fe Alloys | 1.4-1.6 |
| Titanium | 0.9-1.3 |
| Gold | 1.4 |
| Nickel Alloys | 0.3-1.0 |
| Platinum | 0.9 |
| Titanium Carbide | 0.7 |

While not exhaustive, table 1 provides general data for a set of materials. Other metals and metal alloys may also be used.

When lead 310 is at normal temperatures (i.e. normal body temperature of up to about 37° C. to 39° C.) thermal switch 320 is biased such that the contacting portion 380 contacts the outer surface of inner ring 350. In this configuration, outer ring 340 is electrically coupled to inner ring 350.

Conversely, as shown in FIG. 4, when the thermal switch 320 is exposed to increased temperatures (i.e. temperatures at or above about 40° C.), thermal switch 320 is deflected away from inner ring 350. In such embodiments, the side of thermal switch facing inner ring 350 may have a higher coefficient of thermal expansion than the metal used for the side of thermal switch 320 facing outer ring 340.

A variety of metals may be combined to form the bimetallic strip of thermal switch 320. For example, metals having relatively low coefficients of thermal expansion such as tungsten or titanium may be used with metals having higher coefficients of thermal expansion such as gold, silver, or some stainless steel. Other metals and metal alloys may also be used. In some embodiments, the thermal switch is highly responsive to temperature changes. For example, the thermal switch may deflect to de-couple the outer ring 340 and the inner ring 350 within about one minute of the tissue around the electrode heating to a temperature between about 40° C. and 45° C. More preferably, thermal switch 320 may be responsive within less than about 45 to 60 seconds, 30 to 45 seconds, and even more preferably less than about 30 seconds.

Alternatively, thermal switch 320 may comprise a shape memory alloy. Such a material would be designed to transition from a first position in which thermal switch 320 electrically couples outer ring 340 and inner ring 350 to a second position as shown in FIG. 4. Such shape memory alloys include nitinol alloys, but others may be used.

Figure 5:
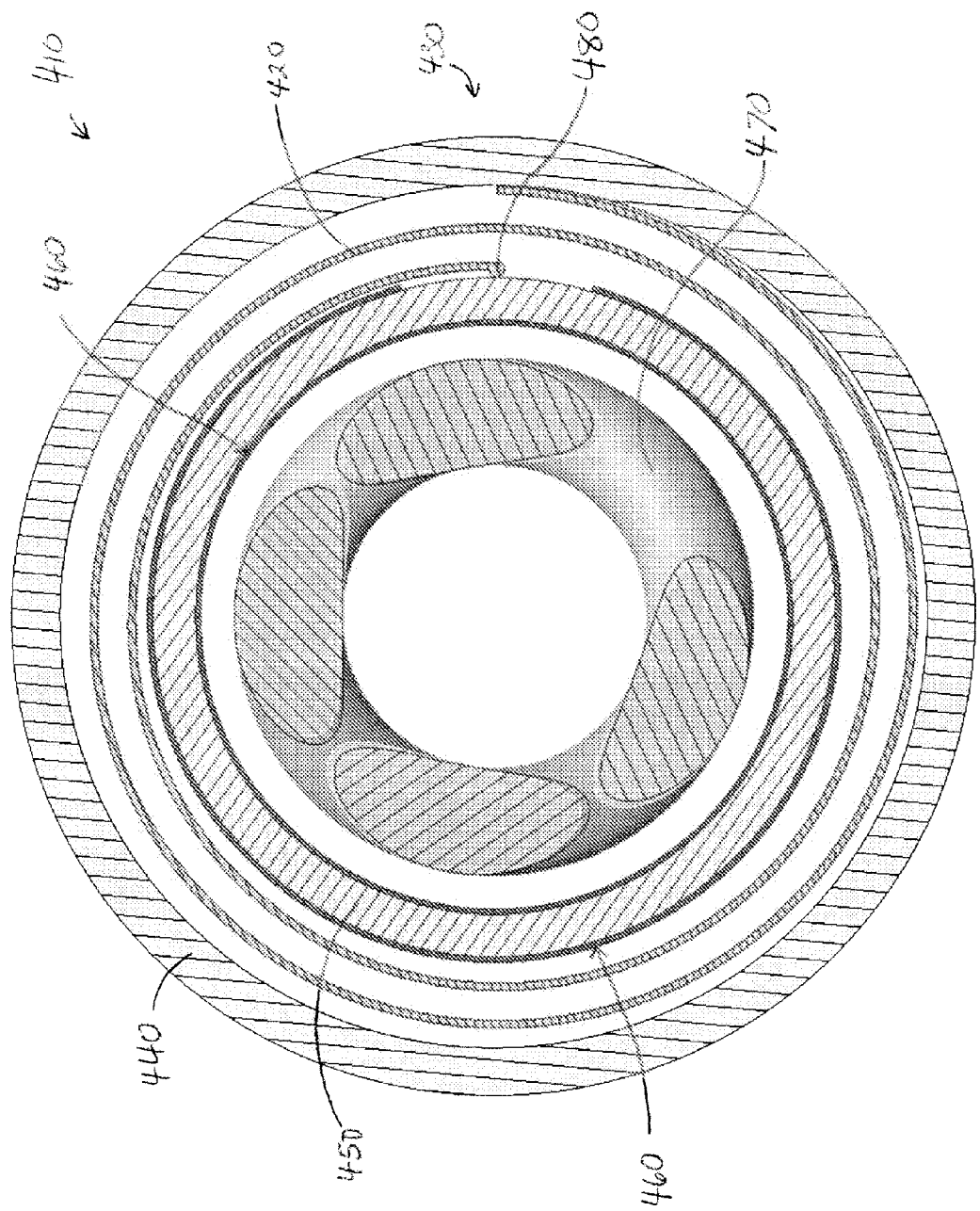
FIG. 5 are radial cross-sectional views of a lead for use in an implantable medical device.
Figure 6:
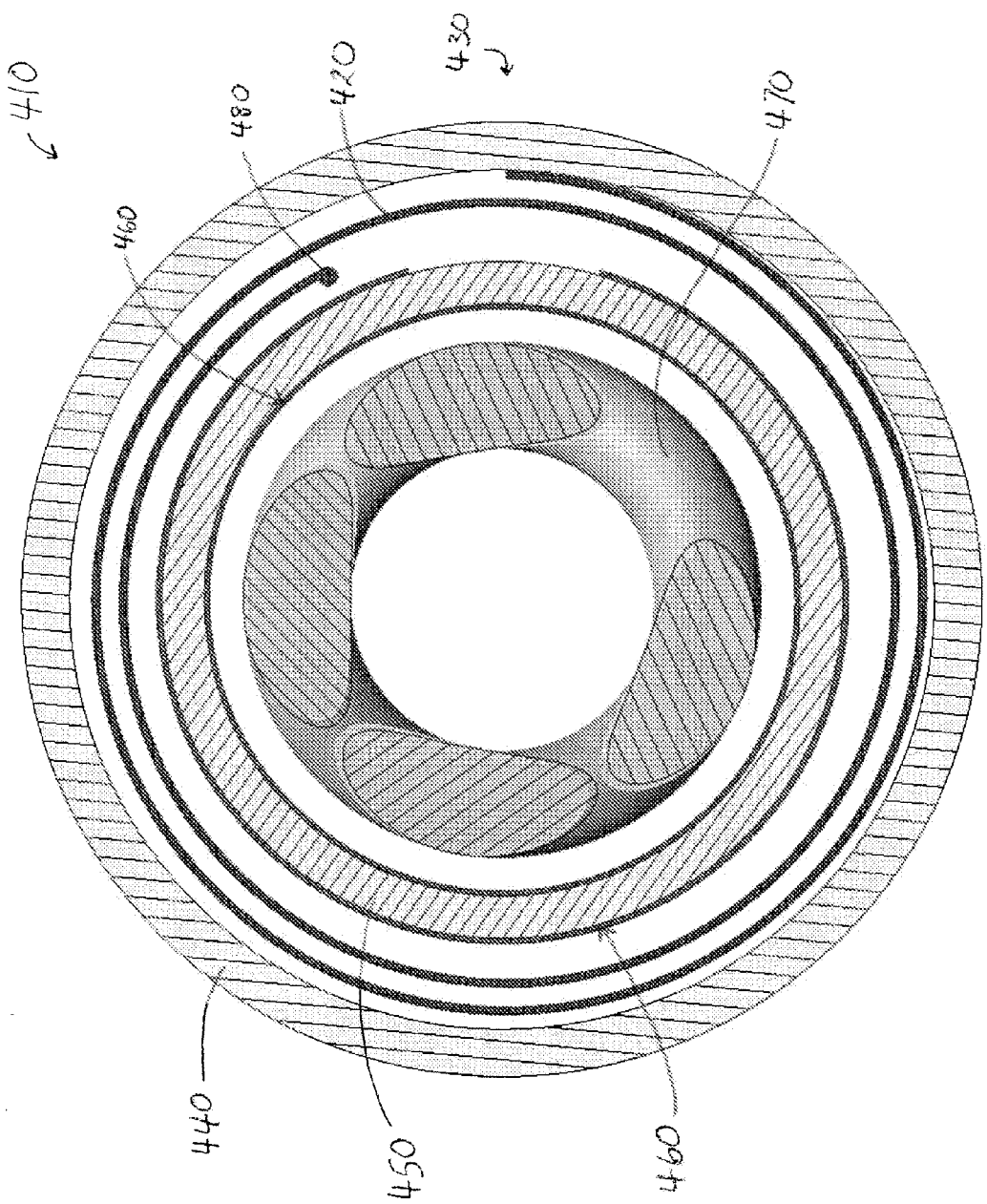
FIG. 6 are radial cross-sectional views of a lead for use in an implantable medical device.

According to another embodiment, FIGS. 5 and 6 illustrate a lead 410 for an implantable medical device including a thermally responsive switch 420. Lead 410 includes an electrode segment 430 comprising an outer ring 440 and an inner ring 450. Inner ring 450 may include an isolating coating 460. Lead filars 470 extend through the lead 410. In the embodiment shown, four lead filars 470 are wound through into a helical shape.

As shown in FIG. 5, thermal switch 420 is fixedly coupled to the inner surface of outer ring 440 and is wound radially in relation to lead 410. Contacting portion 480 is formed on a free end of thermal switch 320 at a point distal to the point where thermal switch 320 is fixedly coupled to the inner surface of outer ring 430. Thermal switch 420 may comprise a bimetallic strip. Thermal switch 420 may be wound about inner ring 450 multiple times to provide thermal switch 420 sufficient length. Generally, the longer thermal switch 420 is, the greater the deflection response will be for a given temperature change. Alternatively, thermal switch 450 may be wound helically to further increase the length of thermal switch 420.

While the medical devices described herein (e.g., systems 200 and 300) are shown and described as a defibrillator and a neurological stimulation device, it should be appreciated that other types of implantable medical devices may be utilized according to other exemplary embodiments, such as pacemakers, cardioverters, cardiac contractility modules, drug administering devices, diagnostic recorders, cochlear implants, and the like for alleviating the adverse effects of various health ailments.

It is also contemplated that the medical devices described herein may be charged or recharged when the medical device is implanted within a patient. That is, according to an exemplary embodiment, there is no need to disconnect or remove the medical device from the patient in order to charge or recharge the medical device.

It is important to note that the construction and arrangement of the implantable device and other structures as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the preferred and other exemplary embodiments without departing from the scope of the present inventions as expressed in the appended claims.

What is claimed is:

1. A generally permanently implantable medical device comprising:
   an electric lead including at least one conductive lead filar and at least one electrode;
   wherein the at least one electrode is electrically coupled to the lead filar by a thermal switch that extends between an inner ring and an outer ring of an electrode segment; and
   wherein the outer ring of the electrode is configured to be in contact with tissue around the electrode, the outer ring surrounds the switch to separate the switch from contact with the tissue, and the switch is responsive to temperature changes of the tissue so as to physically decouple the inner ring and the outer ring.

2. The implantable medical device of claim 1, wherein the thermal switch comprises a bimetallic strip.

3. The implantable medical device of claim 2, wherein the bimetallic strip comprises a metal selected from the group consisting of stainless steel, tungsten, gold, and titanium.

4. The implantable medical device of claim 1, wherein the thermal switch comprises a shape memory alloy.

5. The implantable medical device of claim 4, wherein the shape memory alloy is a nickel titanium alloy.

6. The implantable medical device of claim 5, wherein the nickel titanium alloy has a transition temperature of at least about 38° C. to about 45° C.

7. The implantable medical device of claim 1, wherein the thermal switch is configured to decouple the electrode from the lead filar when the thermal switch reaches a temperature of more than about 38° C.

8. The implantable medical device of claim 1, further comprising a second electrode.

9. The implantable medical device of claim 1, wherein the thermal switch is fixedly coupled to a surface of the outer ring and includes a contact portion for selectively contacting the inner ring.

10. The implantable medical device of claim 1, wherein at least a portion of the inner ring includes an isolating coating.

11. A generally permanently implantable medical device comprising:
    an electronic lead having at least one conductive lead filar and an electrode, the electrode comprising an electrode segment having an inner ring and an outer ring; and
    a switch extending between the inner ring and the outer ring for selectively coupling the electrode to the lead filar, wherein the outer ring of the electrode is configured to be in contact with tissue around the electrode, the outer ring surrounds the switch to separate the switch from contact with the tissue, and the switch is configured to physically decouple the outer ring of the electrode and the lead filar to prevent the electrode from overheating in response to temperature changes of the tissue.

12. The implantable medical device of claim 11, wherein the switch for selectively coupling the electrode to the lead filar comprises a thermal switch.

13. The implantable medical device of claim 11, wherein the switch for selectively coupling the electrode to the lead filar is configured to decouple the electrode from the lead filar when one or more components of the electrode reaches a temperature of more than about 38° C.

14. The implantable medical device of claim 11, wherein the implantable medical device is a neurological stimulation device.

15. The implantable medical device of claim 11, wherein the switch is fixedly coupled to an inner surface of the outer ring.

16. The implantable medical device of claim 11, wherein a portion of the inner ring includes an isolating coating.

17. A system comprising:
    an electric pulse generator;

a generally permanently implantable electric lead coupled to the electric pulse generator including:
- at least one lead filar; and
- an electrode selectively coupled to the lead filar by a thermal switch configured to electrically decouple the lead filar and the electrode, wherein the electrode comprises an electrode segment that includes an outer portion and an inner portion;
- wherein the thermal switch extends between the inner portion and the outer portion; and
- wherein the outer portion of the electrode is configured to be in contact with tissue around the electrode, the outer portion of the electrode surrounds the switch to separate the switch from contact with the tissue, and the switch is responsive to temperature changes of the tissue so as to physically decouple the lead filar and the outer portion of the electrode.

18. The system of claim 17, wherein the thermal switch comprises a bimetallic strip or a shape memory alloy.

19. The system of claim 17, wherein a first end of the thermal switch is fixedly coupled to one of the outer portion and the inner portion and a second end of the thermal switch includes a contact portion for contacting the other of the outer portion and the inner portion.

20. The system of claim 17, wherein the at least one lead filar comprises a plurality of lead filars wound in a helical shape.

* * * * *